United States Patent
Perrut et al.

(10) Patent No.: US 7,291,296 B2
(45) Date of Patent: Nov. 6, 2007

(54) METHOD FOR MAKING VERY FINE PARTICLES CONSISTING OF A PRINCIPLE INSERTED IN A HOST MOLECULE

(75) Inventors: Michel Perrut, Nancy (FR); Jennifer Jung, Nancy (FR); Fabrice Leboeuf, Nancy (FR); Isabelle Fabing, Vandoeuvre-les-Nancy (FR)

(73) Assignee: Separex (Societe Anonyme), Champigneulles (FR)

( * ) Notice: Subject to any disclaimer, the term of this patent is extended or adjusted under 35 U.S.C. 154(b) by 616 days.

(21) Appl. No.: 10/399,595

(22) PCT Filed: Oct. 19, 2001

(86) PCT No.: PCT/FR01/03238

§ 371 (c)(1),
(2), (4) Date: Feb. 17, 2004

(87) PCT Pub. No.: WO02/32462

PCT Pub. Date: Apr. 25, 2002

(65) Prior Publication Data

US 2004/0119179 A1   Jun. 24, 2004

(51) Int. Cl.
*B29B 9/00*   (2006.01)
(52) U.S. Cl. .................... 264/7; 264/5; 264/13; 264/14
(58) Field of Classification Search .................... None
See application file for complete search history.

(56) References Cited

U.S. PATENT DOCUMENTS 5,874,029 A * 2/1999 Subramaniam et al. ....... 264/12
6,461,642 B1 * 10/2002 Bisrat et al. ................. 424/489

FOREIGN PATENT DOCUMENTS

| WO | WO97/31691 | 9/1997 |
| WO | WO99/59710 | 11/1999 |
| WO | WO 00/27844 | 5/2000 |

OTHER PUBLICATIONS

Jung, J. et al. "Particle design using supercritical fluids: Literature and patent survey" Journal of Supercritical Fluids, PRA Press, US, vol. 20, No. 3, Aug. 2001, pp. 179-219.
Kamihira, M. et al. "Formation of inclusion complexes between cyclodextrins and aromatic compounds under pressurized carbon dioxide" J Ferment Bioeng, 1990 69 (6) pp. 350-353.

(Continued)

*Primary Examiner*—Mary Lynn Theisen
(74) *Attorney, Agent, or Firm*—Young & Thompson

(57) ABSTRACT

The invention concerns a method for making very fine particles containing at least an active principle inserted in a host molecule and a device for implementing said method. The method is characterized in that it consists in forming a solution of the active principle in a first liquid solvent and of a product formed by the host molecules in a second liquid solvent, then in contacting the resulting solutions with a supercritical pressure fluid, so as to precipitate the host molecules which are dissolved therein.

15 Claims, 1 Drawing Sheet

OTHER PUBLICATIONS

Figure 1:
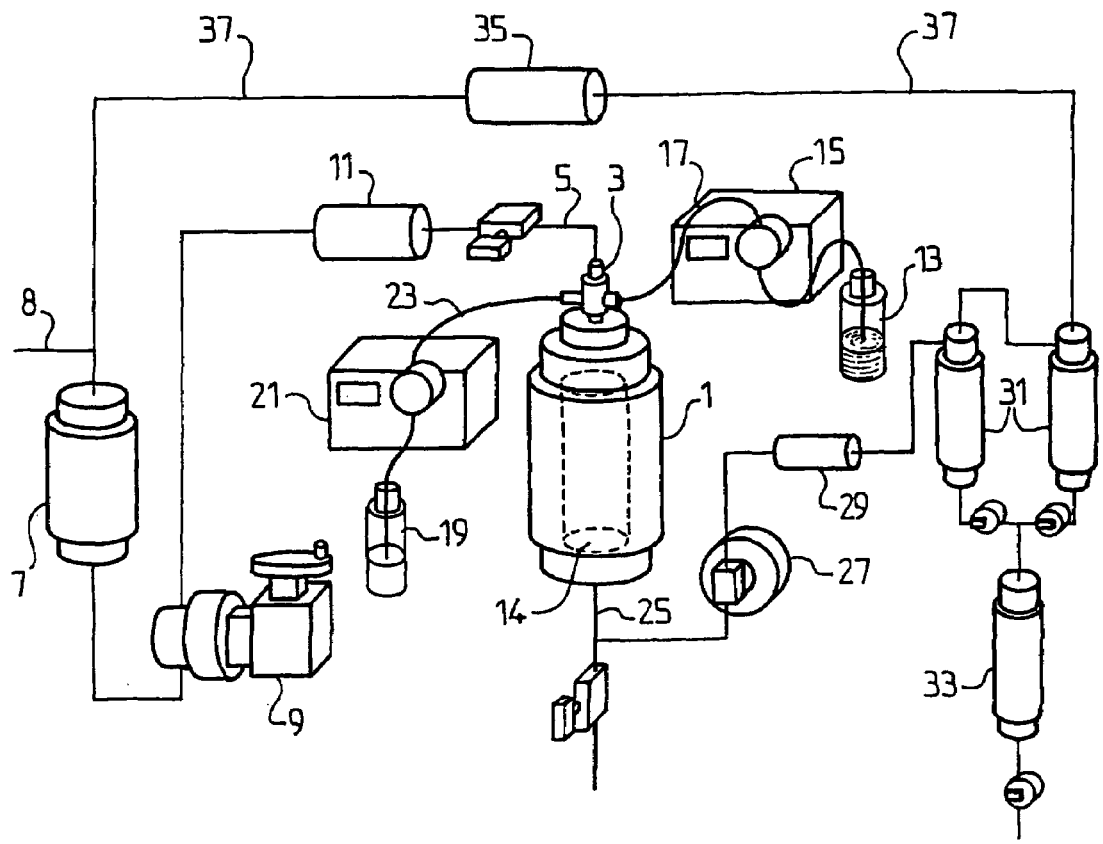

Subrananiam, B. et al. "Pharmaceutical processing with supercritical carbon dioxide" Journal of Pharmaceutical Sciences, US, vol. 86, No. 8, Aug. 1, 1997 pp. 885-890.

Van Hees, T. et al. "Application of supercritical carbon dioxide for the preparation of a piroxicam-beta-cyclodextrin inclusion compound" Pharmaceutical Research Dec. 1999 16 (12) 1864-1870.

Van Hees, T. et al. "Inclusion of piroxicam into beta- cyclodextrin by means of supercritical carbon dioxide: thermal, spectroscopic and physicochemical studies" Journal de Pharmacie de Belgique (Jan.-Feb. 2000) 55 (1) pp. 30-31.

* cited by examiner

METHOD FOR MAKING VERY FINE PARTICLES CONSISTING OF A PRINCIPLE INSERTED IN A HOST MOLECULE

The present invention relates to a method for making very fine particles constituted by at least one active principle inserted in a "host" molecule, particularly of cyclodextrin type, as well as to a device for carrying out this method. The present invention also concerns the particles thus produced.

It is known that the pharmaceutical industry, but also the cosmetics industry and agrochemicals, are seeking novel formulations in order to improve the efficiency of certain molecules of therapeutic, dermatological or plant protective interest. These industries are also searching for means making it possible to increase the solubility in the biological media of insoluble, or very sparingly soluble, active principles, in order to increase their bio-availability, to reduce the doses administered and therefore to reduce the secondary effects. They are also seeking to avoid the loss of biological activity due to the problems of instability in the aqueous media or during storage in the presence of oxygen, of humidity of the air or of light. With a view to solving these problems, it has been proposed to use different excipients, but without arriving at satisfactory solutions.

Various methods have been proposed for making fine particles constituted by an active principle which is inserted in a matrix, in order to protect it against various physical or chemical degradations, or to facilitate its solubilization in aqueous solutions.

For some years, novel host molecules have been called upon, which are adapted to form a molecular complex in which they enclose a molecule of an active principle. Host molecules of cyclodextrin type are for example known, whose development in the pharmaceutical industry is promising at the present time. These molecules, of natural origin, issuing from the enzymatic degradation of starch, are produced industrially and present the advantage of being biodegradable. Cyclodextrins are natural host molecules whose cyclic form allows them to "capture" a large variety of solid, liquid or gaseous substances leading to the formation of "supermolecules".

Advantage is generally taken of such a "capture" of the active principles in order to modify the physico-chemical properties of the molecules captured and in particular their solubility, their stability and their reactivity. Moreover, numerous chemical groups (methyl-, hydroxypropyl-, carboxymethyl-, acetyl-) may be grafted on the natural cyclodextrins by reaction with the hydroxyl groups, modifying the interactions with the trapped substances. The random position and type of substitution render these so-called "modified" cyclodextrins amorphous, this contributing to considerably increasing their solubility in water and in organic solvents. Methyl-β-cyclodextrin may thus be cited, which is very soluble in water (3000 g/l), while not being hygroscopic; it does not change the surface tension of the water where it is dissolved and it is also soluble in methanol and ethanol. Moreover, it is admitted that this molecule may be used in oral, parenteral, nasal, transdermal, vaginal or rectal administration.

The present invention concerns a novel method making it possible to effect the insertion at the molecular level of an active principle, particularly of pharmaceutical, cosmetological, dietetic or plant protective interest, in a host molecule particularly of cyclodextrin or modified cyclodextrin type and to make fine particles of this molecular complex, using a method employing a supercritical pressure fluid.

It will firstly be recalled that bodies are generally known in three states, namely solid, liquid or gaseous, and that one passes from one to the other by varying the temperature and/or the pressure. Now, there exists a point beyond which one can pass from the liquid state to the state of gas or vapour without passing through a boiling or, inversely, through a condensation, but in continuous manner. This point is called the critical point.

It is also known that a fluid in supercritical state is a fluid which is in a state characterized either by a pressure and a temperature respectively greater than the critical pressure and temperature in the case of a pure body, or by a representative point (pressure, temperature) located beyond the envelope of the critical points represented on a diagram (pressure, temperature) in the case of a mixture. Such a fluid presents, for numerous substances, a high solvent power with no comparison to that observed in this same fluid in the state of compressed gas.

The same applies to so-called "subcritical" liquids, i.e. liquids which are in a state characterized either by a pressure higher than the critical pressure and by a temperature lower than the critical temperature in the case of a pure body, or by a pressure higher than the critical pressures and a temperature lower than the critical temperatures of the components in the case of a mixture (cf. Michel PERRUT—Les techniques de l'Ingénieur "Extraction par fluide supercritique (*Engineering Techniques "Extraction by supercritical fluid*), J 2 770-1 to 12, 1999"). In the following description, "supercritical pressure fluid" will designate a fluid taken to a pressure higher than its critical pressure, whether it is in supercritical or subcritical state as defined hereinabove.

The considerable and modulatable variations of the solvent power of supercritical pressure fluids are, moreover, used in numerous methods of extraction (solid/fluid), of fractioning (liquid/fluid), of analytical or preparative chromatography, of treatment of materials (ceramics, polymers), of generation of particles, or as medium for carrying out chemical or biochemical reactions. It should be noted that the physico-chemical properties of carbon dioxide as well as its critical parameters (critical pressure: 7.4 MPa and critical temperature: 31° C.), make of it a preferred solvent in numerous applications, all the more so as it does not present any toxicity and is available in very large quantities at very low cost. Other fluids may also be used under similar conditions, such as nitrogen protoxide, light hydrocarbons having two to four carbon atoms, and certain halogenated hydrocarbons.

It is known from numerous Patents and scientific publications that supercritical pressure fluids, and particularly supercritical carbon dioxide, are widely used to make very fine powders of "micronic" or "submicronic" sizes capable of dissolving very rapidly or which can be used by ingestion via the respiratory tracts. Fluids at supercritical pressure are also studied with a view to obtaining very fine complex particles formed by mixtures of different morphologies of the active principle and of an excipient.

The majority of the systems described in the Patents and publications are applied to an encapsulation of matricial type, which consists in integrating an active substance in a support particularly of alginate, cellulosic derivatives, waxes, triglycerides, polysaccharides, or acrylic polymers type. Microspheres will be distinguished, which are constituted by an active principle dispersed within an excipient of the microcapsules, which are composed of a core of active substance surrounded by a continuous envelope.

The so-called "RESS" technique (Debenedetti P., Journal of Controlled Release, 24, 1993, p. 27-44—Debenedetti P., Journal of Supercritical Fluids, 7, 1994, p. 9-29) is based on forming a solution of the active principle and of the excipient in the supercritical pressure fluid. The atomization of this supercritical solution allows the formation of microspheres. However, this technique is limited by the weak solubility of the majority of the polymers and active substances in the supercritical fluids.

The so-called anti-solvent methods, known under the designations "SAS, SEDS, PCA or ASES" allow the formation of composite micro-particles. They describe the contacting of organic solutions of active principles and of excipient with a supercritical fluid. Different Patents describe various means for contacting the different fluids: Introduction of the supercritical fluid in the organic solution (U.S. Pat. No. 5,360,478), separate spraying of the organic solution and of the supercritical fluid (Patents DE-A-3 744 329, U.S. Pat. No. 5,043,280), use of coaxial nozzles with two or three inlets (Patents WO 95/01221, WO 96/00610).

As for the so-called "PGSS" method, it allows the encapsulation of active principles by spraying at low pressure of a mixture of active principle/excipient saturated by a supercritical fluid (Patents EP-A-0744992, WO 95/21688).

The supercritical fluids thus make it possible to produce an encapsulation of membrane type by inclusion of active principles in liposomes (U.S. Pat. No. 5,700,482).

The present invention has for an object to propose a method for the preparation of fine particles constituted by at least one active principle, insoluble or very sparingly soluble in aqueous solutions, and which is dispersed in molecular form in host molecules of cyclodextrin type, using a supercritical pressure fluid. This method makes it possible to avoid, or to reduce to acceptable quantities from the toxicological standpoint, the organic solvent residues present in the particles obtained.

More particularly, this method makes it possible to prepare fine particles of active principle, insoluble or very sparingly soluble in aqueous solutions, and which are inserted in a host molecule of cyclodextrin type. In the case of the formulation of pharmaceutical products, these particles present an increased bio-availability of the active principle, and this whatever the mode of administration.

The present invention thus has for an object a method for making very fine particles containing at least one active principle, these particles being formed by an assembly of molecular complexes each constituted by a molecule of active principle inserted in a host molecule, characterized in that it comprises the steps consisting in:
    forming a solution of the active principle in a first liquid solvent and a product formed by the host molecules in a second liquid solvent,
    contacting the liquid solutions thus formed with a supercritical pressure fluid, so as to reduce the solvent power of the liquid solvents and to cause the host molecules which are dissolved therein to precipitate, by anti-solvent effect,
    extracting the residual solvents by means of a supercritical pressure fluid and evacuating the fluid/solvents mixture,
    recovering the particles thus generated in the form of dry powder.

In a form of embodiment of the method according to the invention, in which the active principle is soluble in the supercritical pressure fluid, the latter may be used as solvent. Saturation of the supercritical pressure fluid will preferably be ensured by causing it to percolate through a bed of particles of at least one active principle.

The present invention thus has for an object a method for making very fine particles containing at least one active principle, these particles being formed by an assembly of molecular complexes each constituted by a molecule of active principle inserted in a host molecule, characterized in that it comprises the steps consisting in:
    forming a solution of the active principle in a first liquid solvent constituted by a supercritical pressure fluid and a product formed by the host molecules in a second liquid solvent,
    contacting the liquid solutions thus formed, so as to reduce the solvent power of the liquid solvents and to cause the host molecules which are dissolved therein to precipitate, by anti-solvent effect,
    extracting the residual solvents by means of a supercritical pressure fluid and evacuating the fluid/solvents mixture,
    recovering the particles thus generated in the form of dry powder.

In a form of embodiment of the invention, the first and second solvents will be identical. The formation of solution of the active principle and of the product formed by the host molecules and the contacting of the solutions may also be effected during the same step.

According to the invention, the host molecule may be constituted by at least one cyclodextrin of the α-cyclodextrine, or β-cyclodextrine or γ-cyclodextrin type. It may also be constituted by at least one cyclodextrin modified by grafting of a chemical group, particularly of methyl-α-cyclodextrin, hydroxypropyl-α-cyclodextrin, methyl-β-cyclodextrin, hydroxypropyl-β-cyclodextrin, carboxymethyl-β-cyclodextrine, or acetyl-β-cyclodextrin type.

The present invention also has for an object a device for making very fine particles comprising at least one active principle inserted in a host molecule, characterized in that it comprises an atomization chamber of which the upper part is provided with spraying means which are supplied on the first hand with a liquid solution of at least one active principle, on the second hand with a liquid solution of a matrix of cyclodextrin, and on the third hand with a supercritical pressure fluid, the lower part of the atomization chamber is provided with means for recovering the microparticles formed and with an outlet for the supercritical pressure fluid which is connected to separation means, particularly of cyclonic type, and drawing-off elements allowing a recycling of the fluid towards a storage tank.

The spraying means may be constituted by a nozzle allowing the simultaneous introduction of the solution of at a least one active principle, and of the liquid solution of cyclodextrine matrix. In a form of embodiment of the invention, the nozzle will, in addition, allow the simultaneous introduction of the supercritical pressure fluid. This spraying nozzle may comprise an inner collector volume in which converge upstream channels in communication with the fluids which it is desired to spray in the atomization chamber and an outlet channel in communication with the atomization chamber.

The present invention also has for an object a product constituted by very fine particles containing at least one active principle, characterized in that these particles are formed by an assembly of molecular complexes each constituted by a molecule of active principle inserted in a host molecule.

In the usual configuration, the method makes it possible to introduce, separately, a solution of an active principle or of a mixture of active principles, a solution of host molecules of cyclodextrin type, and a supercritical pressure fluid, the formation of the complex of the active principle or principles and of the matrix taking place in a recipient under pressure, during the precipitation phase.

According to a variant, the active principle, or the mixture of active principles, and the product formed by the host molecules, particularly of cyclodextrin type, are dissolved in the same liquid solvent, and these solutions may be introduced in mixture in the recipient under pressure swept by the supercritical pressure fluid; in this case, the active principle(s)/host molecule complex may be formed before the contacting with the supercritical pressure fluid or during the precipitation phase.

The inserted particles will preferably have a diameter included between 0.01 μm and 30 μm and will be constituted in particular by an active principle of alimentary, pharmaceutical, cosmetic, agrochemical or veterinary interest. Furthermore, and although another gas may be used, the supercritical pressure fluid will favourably be constituted by carbon dioxide, possibly having a volatile organic solvent, of light hydrocarbon, alcohol, ester, ketone or halocarbon type, added thereto. Whatever their diameter, these particles will be designated in the present text by fine particles.

It will be noted that the supercritical pressure fluid laden with organic solvents may be recycled in accordance with the methods conventionally used in supercritical extraction/fractioning, in particular by using devices of the type such as those described in French Patent FR-A-2 584 618.

On the other hand, the contacting of the active principle/host molecule complex and of a supercritical pressure fluid makes it possible to effect simultaneously the precipitation and the drying of the particles under mild conditions, which makes of it a choice technique for encapsulation of fragile products, such as for example proteins.

From a practical standpoint, the contacting of the supercritical fluid with the solution(s) of active principle(s) and of host molecule is either effected by introduction of the supercritical pressure fluid in an autoclave already containing the solution, or by spraying of the solution(s) through one or more nozzles in an autoclave swept by supercritical pressure fluid. The nozzles used may present different configurations: separate inlets of the solution or the solutions and the supercritical fluid, or single inlet allowing the contacting of the two fluids just in front of the orifice of the nozzle so that the speed of the supercritical fluid makes it possible to spray the liquid solution in very fine droplets.

Various forms of embodiment of the present invention will be described hereinafter by way of non-limiting example with reference to the accompanying drawing, in which:

FIG. 1 schematically shows an installation for producing fine particles of at least one active principle encapsulated in a host molecule of cyclodextrin type, according to the invention.

Figure 2:
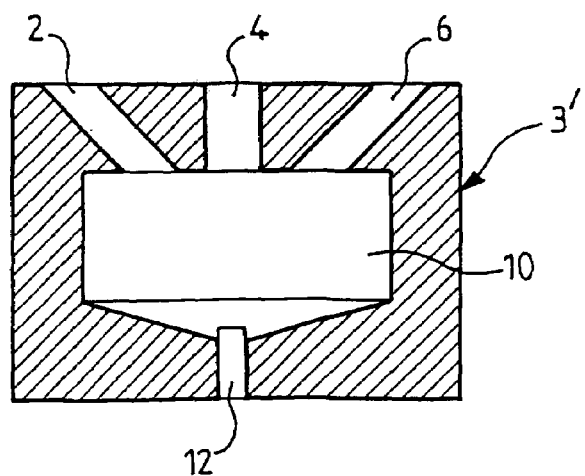

FIG. 2 is a view in axial section of an example of implementation of a spraying nozzle used in the device according to the invention.

This device is essentially constituted by an atomization chamber 1 of which the upper part is provided with a spraying nozzle 3 which is supplied with liquefied gas via a pipe 5 connected to a storage tank 7. A pump 9 and an exchanger 11 make it possible to take the liquefied gas to supercritical state. The solution of the active principle, or of the mixture of active principles, in an organic or aqueous solvent is contained in a recipient 13 and is taken to the spraying nozzle 3 via a conduit 17 under the action of a pump 15. Similarly, the solution of host molecule, particularly of cyclodextrin or modified cyclodextrin type, in an organic or aqueous solvent is contained in a recipient 19 and is taken to the spraying nozzle 3 via a conduit 23 under the action of a pump 21. The lower part of the atomization chamber 1 is provided with an outlet of the supercritical pressure fluid 25 which is connected to cyclonic separators 31 via a regulation valve 27 and a filter 29. The outlet of the separators 31 is connected to drawing-off elements 33. The last separator 31 is connected to the storage tank 7 by a conduit 37 traversing a condenser 35.

According to the invention, there are simultaneously injected into the atomization chamber 1 the solutions of active principle, or of the mixture of active principles contained in the recipient 13, the solution of the host molecule, contained in the recipient 19, and the gas contained in the tank 7 which is taken to the supercritical state by the pump 9 and the exchanger 11.

In the course of this operation, the flux of supercritical pressure fluid entrains the solvent in which is dissolved the active principle and the host molecule in the form of complex or not, which has the effect of increasing their concentration beyond saturation, thus provoking the precipitation of the products in complexed form. The fine particles obtained are separated from the supercritical fluid, containing the organic or aqueous solvents, by passage through a filtering element 14, disposed at the bottom of the atomization chamber 1, and which is constituted for example by a disc of sintered metal or by a woven or non-woven textile.

At the outlet of the atomization chamber 1, the solvent-laden fluid is partially expanded to the pressure of recycling through the regulation valve 27 and reheated in cyclonic separators 31 after filtration through the filter 29.

The collected solvent is drawn off in liquid phase at atmospheric pressure by the drawing-off elements 33. The fluid, from which the major part of the solvent has been removed, is recycled by liquefaction in the condenser 35 towards the tank of liquid fluid 7. The addition of fluid in the liquid or gaseous state is effected via an inlet 8.

According to an interesting variant of the invention, particularly favourable to obtaining particles of very small diameter, the solutions of active principle and of the host molecule as well as the supercritical pressure fluid are introduced through a single nozzle 3' particularly of the type such as that shown in FIG. 2 and which will be described hereinafter.

When the quantity of fine particles fixed on the filtering element 14 is sufficient, the pumping of the solutions of active principle and of host molecule is interrupted. The small quantities of solvent present in the fine particles may then be eliminated by causing a stream of carbon dioxide in the supercritical state to percolate through the bed of these particles deposited on the filtering element 14. After total elimination of this solvent, the atomization chamber 1 is depressurized and the fine particles recovered on the filtering element 14.

In a variant embodiment of the invention, the active principle, or the mixture of active principles, and the product constituted by host molecules are dissolved in the same solvent. In this form of embodiment, one sole pump 15 or 21 is in that case necessary for injecting the solution in the atomization chamber 1 by means of the spraying nozzle 3.

The spraying nozzle 3' shown in FIG. 2 is constituted by a cylindrical metal pellet of which the upstream principal face is hollowed out with three channels 2, 4, 6, which converge in a collector chamber 10 and which ensure supply thereof with solution of active principle, with solution of host molecule as well as with supercritical pressure fluid.

The latter is itself in communication with the downstream outlet of the nozzle 3' via an axial pipe 12.

In order to illustrate the present invention, the following examples of embodiment will be cited, employed on an installation of semi-industrial size having a service pressure of 30 MPa and a temperature range going from 0° C. to 150° C., constructed in accordance with the diagram shown in FIG. 1.

Carbon dioxide was used as supercritical pressure fluid. The diaphragm pump 9 allowed a flowrate of the order of 6 kg/hr. to 20 kg/hr. of carbon dioxide under a pressure of 30 MPa, the solution supply pumps 15 and 21 allowed a flowrate of 0.05 kg/hr to 0.75 kg/hr. of liquid at 30 Mpa, the fluid tank 7 having a total volume of 2 liters, the atomization chamber 1 being constituted by a tubular recipient of vertical axis, of diameter 0.1 m and with a total volume of 4 liters, provided on its section, at the bottom of the recipient, with a filtering element 14 constituted by a membrane of non-woven glass microfibers with a porosity of 0.7 µm supported by a disc of sintered metal with a porosity of 50 µm.

EXAMPLE 1

By means of the installation thus described, there was generated a powder of very fine particles of complex formed by a steroid, prednisolone, and by methyl-β-cyclodextrin, by spraying a solution containing 0.32% by mass of prednisolone and 2.5% by mass of methyl-β-cyclodextrin, viz. a mol ratio of 1:2, in absolute ethanol with a flowrate of 0.5 kg/hr. in a stream of 15 kg/hr. of carbon dioxide at 15 MPa and 40° C. The active principle and the matrix being formed in solution in the ethanol concomitantly, only one pump 15 for introduction in the atomization chamber 1 was used. This liquid solution and the supercritical pressure fluid were introduced in the chamber 1 via a single nozzle 3', the two fluids mixing in the cavity 10 with a volume close to 0.5 ml made in the body of the nozzle 3', placed in communication with the atomization chamber 1 via the conduit 12 provided with an orifice with a diameter of 0.06 mm.

After an hour of spraying, the introduction of solution of active principle was stopped and a stream of carbon dioxide at 15 MPa and at 40° C. was made to percolate in the bed of particles fixed on the filtering element. The carbon dioxide was then sent towards the separators where the organic solvent was recovered. After depressurization of the atomization chamber 1, the micro-particles fixed on the filtering element 14 were recovered.

The characteristics of the recovered fine particles are the following:
- granulometric distribution: 90% of the particles have a diameter included between 0.8 µm and 3.5 µm and a mean diameter of 1.4 µm.
- composition by mass: 11% of prednisolone and 85% of methyl-β-cyclodextrin.

The content of organic solvent in the fine particles, determined by gaseous phase chromatography of the aqueous phase obtained by prolonged stirring of the powder under ultrasounds, is less than 100 ppm, which allows the use of these particles without supplementary treatment.

EXAMPLE 2

By means of the installation described hereinbefore, there was generated a powder of very fine particles of complex formed by an anti-inflammatory, ibuprofen, and by methyl-β-cyclodextrin, by spraying a solution containing 0.22% by mass of ibuprofen and 3.0% by mass of methyl-β-cyclodextrin, viz. a mol ratio of 1:2, in acetone with a flowrate of 0.5 kg/hr. in a stream of 15 kg/hr. of carbon dioxide at 15 MPa and 40° C. After an hour of spraying, the introduction of solution of active principle was stopped and a stream of carbon dioxide at 15 MPa and at 40° C. is made to percolate in the bed of particles fixed on the filtering element. The carbon dioxide was then sent towards the separators where the organic solvent was recovered. After depressurization of the atomization chamber, the fine particles fixed on the filtering element 14 were recovered.

The characteristics of the recovered fine particles are the following:
- granulometric distribution: 90% of the fine particles have a diameter included between 0.7 µm and 2.9 µm and a mean diameter of 1.1 µm.
- composition by mass: 8% of ibuprofen and 92% of methyl-β-cyclodextrin.

The content of organic solvent in the fine particles, determined by gaseous phase chromatography of the aqueous phase obtained by prolonged stirring of the powder under ultrasounds, is less than 100 ppm, which allows the use of these fine particles without supplementary treatment.

It has been observed that, although the host molecules which prove most interesting are cyclodextrins and modified cyclodextrins, it is possible according to the invention to call upon other types of host molecules such as in particular ring ethers.

The invention claimed is:

1. A method for making very fine particles containing at least one active principle, wherein the particles comprise an assembly of molecular complexes having a molecule of an active principle within a host molecule, said method comprising
   forming a solution of the active principle in a first solvent and a solution with a product formed by the host molecules in a second solvent,
   contacting the liquid solutions thus formed with a first supercritical pressure fluid, causing the host molecules to precipitate,
   extracting the residual solvents by means of a second supercritical pressure fluid and evacuating the fluid/solvents mixture,
   recovering the particles thus generated in the form of dry powder.

2. A method for making very fine particles containing at least one active principle, wherein the particles comprise an assembly of molecular complexes having a molecule of an active principle within a host molecule, said method comprising
   forming a solution of the active principle in a first solvent comprising a third supercritical pressure fluid and a solution with a product formed by the host molecules in a second solvent, precipitating the host molecules,
   extracting the residual solvents by means of a second supercritical pressure fluid and evacuating the fluid/solvents mixture,
   recovering the particles thus generated in the form of dry powder.

3. The method according to claim 2, wherein the third supercritical pressure fluid is saturated with the active principle before it is formed in a liquid solution.

4. The method according to claim 3, wherein saturation of the third supercritical pressure fluid solvent with the active principle is obtained by causing it to percolate through a bed of particles of at least one active principle.

5. The method according to claim 1, wherein the first and second solvents are identical.

6. The method according to claim 5, wherein the formation of solution of the active principle and a solution with a product formed by the host molecules and the contacting of the solutions thus formed are effected simultaneously.

7. The method according to claim 1, wherein the first supercritical pressure fluid is carbon dioxide.

8. The method according to claim 1, wherein the host molecule comprises a cyclodextrin selected from the group consisting of α-cyclodextrin, β-cyclodextrine and γ-cyclodextrin.

9. The method according to claim 1, wherein the host molecule comprises at least one modified cyclodextrin selected from the group consisting of methyl-α-cyclodextrin, hydroxypropyl-α-cyclodextrin, methyl-β-cyclodextrin, hydroxypropyl-β-cyclodextrin, carboxymethyl-β-cyclodextrine, and acetyl-β-cyclodextrin.

10. The method according to claim 1, wherein the host molecule comprises at least one cyclodextrin modified by grafting of a chemical group.

11. The method according to claim 1, wherein the active principle selected from the group consisting of pharmaceutical actives, cosmetological actives, dietetic actives and plant-protective actives.

12. A method for making fine particles containing at least one active principle, wherein the particles comprise an assembly of molecular complexes having an active principle within a host molecule, said method comprising forming a first solution comprising the active principle and a first solvent, forming a second solution comprising the host molecules and a second solvent, contacting the first and second liquid solutions with a first supercritical pressure fluid, causing the host molecules to precipitate, extracting the residual solvents by means of a second supercritical pressure fluid and evacuating the fluid/solvents mixture, recovering the particles thus generated in the form of dry powder, and wherein the host molecule comprises a cyclodextrin selected from the group consisting of α-cyclodextrin, β-cyclodextrine, γ-cyclodextrin, methyl-α-cyclodextrin, hydroxypropyl-α-cyclodextrin, methyl-β-cyclodextrin, hydroxypropyl-β-cyclodextrin, carboxymethyl-β-cyclodextrine, and acetyl-β-cyclodextrin.

13. the method according to claim 12, wherein the first and second solvents are identical.

14. The method according to claim 12, wherein the first supercritical pressure fluid is carbon dioxide.

15. The method according to claim 12, wherein the active principle selected from the group consisting of pharmaceutical actives, cosmetological actives, dietetic actives and plant-protective actives.

* * * * *